(12) United States Patent
Yang et al.

(10) Patent No.: US 8,404,000 B2
(45) Date of Patent: Mar. 26, 2013

(54) ORGANIC DYE, COMPOSITE DYE AND DYE-SENSITIZED SOLAR CELLS USING THE SAME

(75) Inventors: Cheng-Hsien Yang, Tainan County (TW); Hao-Hsun Yang, Tainan (TW); Wen-Fa Kuo, Tainan (TW); Wei-Ting Wang, Tainan County (TW)

(73) Assignee: Industrial Technology Research Institute, Hsinchu County (TW)

( * ) Notice: Subject to any disclaimer, the term of this patent is extended or adjusted under 35 U.S.C. 154(b) by 348 days.

(21) Appl. No.: 12/905,022

(22) Filed: Oct. 14, 2010

(65) Prior Publication Data
US 2012/0090684 A1    Apr. 19, 2012

(51) Int. Cl.
*A61Q 5/10*  (2006.01)
*C07D 255/04*  (2006.01)

(52) U.S. Cl. .................................. 8/637.1; 548/255
(58) Field of Classification Search .................. 8/637.1; 548/255
See application file for complete search history.

(56) References Cited

FOREIGN PATENT DOCUMENTS
JP    2005222942 A    8/2005

OTHER PUBLICATIONS

STIC Search Report dated Oct. 24, 2012.*
Basham et al., "Foerster Resonance Energy Transfer in Dye-Sensitized Solar Cells", ACS Nano, vol. 4, No. 3, 1253-1258 (2010).
Cid et al., "Molecular Cosensitization for Efficient Panchromatic Dye-Sensitized Solar Cells", Angew. Chem. 119, 8510-8514 (2007).
Choi et al., "Stepwise Cosensitization of Nanocrystalline TiO2 Films Utilizing Al2O3 Layers in Dye-Sensitized Solar Cells", Angew. Chem., 120, 8383-8387 (2008).
Planells, "The effect of molecular aggregates over the interfacial charge transfer processes on dye sensitized solar cells", Applied Physics Letters, 92, 153506 (2008).
Rocca, "Time-Dependent Density Functional Perturbation Theory: New algorithms with applications to molecular spectra", Ph.D. Thesis, Oct. 2007.
Lin et al., "Design and Characterization of Novel Porphyrins with Oligo(phenylethylnyl) Links of Varied Length for Dye-Sensitized Solar Cells: Synthesis and Optical, Electrochemical, and Photovoltaic Investigation", J. Phys. Chem. C 2009, 113, 755-764 (2009).
Hayashi et al., "Naphthyl-Fused Π-Elongated Porphyrins for Dye-Sensitized TiO2 Cells", J. Phys. Chem. C 2008, 112, 15576-15585 (2008).
Li et al., "Phthalocyanines and Their Analogs Applied in Dye-Sensitized Solar Cell", Struct Bond, 135:229-274 (2010).

* cited by examiner

*Primary Examiner* — Eisa Elhilo
(74) *Attorney, Agent, or Firm* — Pai Patent & Trademark Law Firm; Chao-Chang David Pai

(57) ABSTRACT

The invention provides an organic dye, a composite dye and dye-sensitized solar cell using the same. The organic dye has Formula (I):

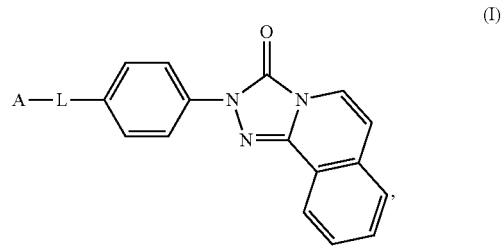

wherein L is a linker group and comprises a substituted or unsubstituted $C_4$-$C_{20}$ aryl group, a substituted or unsubstituted heteroaryl group, a substituted or unsubstituted carboncyclic group, a substituted or unsubstituted heterocyclic group or combinations thereof, and A is an electron acceptor group.

18 Claims, 3 Drawing Sheets

ORGANIC DYE, COMPOSITE DYE AND DYE-SENSITIZED SOLAR CELLS USING THE SAME

BACKGROUND OF THE INVENTION

1. Field of the Invention

The present invention relates to an organic dye, and in particular relates to an organic dye used in dye-sensitized solar cells (DSSCs).

2. Description of the Related Art

Development in the solar cell industry is driven by global environmental concerns and rising raw material prices. Among the various solar cells developed, dye-sensitized solar cell (DSSC) is advantageous as it can be fabricated with relatively lower costs due to its simpler fabrication process and suitability for large area fabrication.

There are two kinds of dye used in DSSCs, one is large organic molecules (such as coumarin, cyanine), the other is ruthenium (Ru) metal complexes. The performances of DSSCs based on large organic molecules are usually insufficient. On the other hand, ruthenium (Ru) metal complexes have better performance, but its molar absorption coefficient at short wavelength regions (about 350 nm-500 nm) is lower than that of large organic molecules.

Thus, there is a need to develop an organic dye which has high molar absorption coefficient in short wavelength regions. If such an organic dye and ruthenium (Ru) metal complexes are used together, the photoelectric conversion efficiency of DSSC should be improved.

BRIEF SUMMARY OF THE INVENTION

The invention provides an organic dye which has a Formula (I):

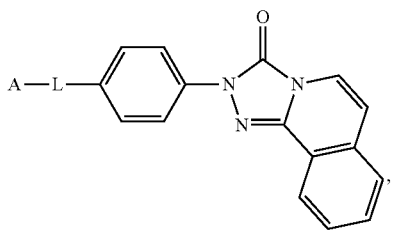

wherein L is a linker group and comprises a substituted or unsubstituted $C_4$-$C_{20}$ aryl group, a substituted or unsubstituted heteroaryl group, a substituted or unsubstituted carboncyclic group, a substituted or unsubstituted heterocyclic group or combinations thereof, and A is an electron acceptor group.

The invention also provides a composite dye, comprising a composite dye which comprises ruthenium metal complexes and an organic dye having a Formula (I):

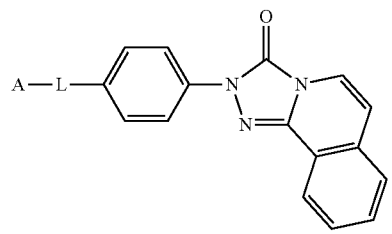

wherein L is a linker group and comprises a substituted or unsubstituted $C_4$-$C_{20}$ aryl group, a substituted or unsubstituted heteroaryl group, a substituted or unsubstituted carboncyclic group, a substituted or unsubstituted heterocyclic group or combinations thereof, and A is an electron acceptor group.

The invention also provides a dye-sensitized solar cell comprising: a first electrode, wherein the first electrode comprises a composite dye and the composite dye comprises: ruthenium metal complexes; and an organic dye having Formula (I):

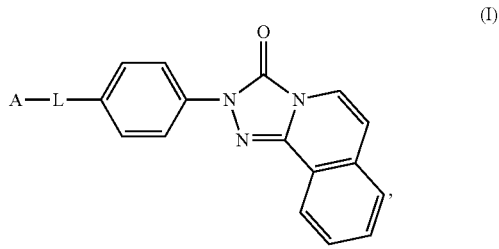

wherein L is a linker group comprising a substituted or unsubstituted $C_4$-$C_{20}$ aryl group, a substituted or unsubstituted heteroaryl group, a substituted or unsubstituted carboncyclic group, a substituted or unsubstituted heterocyclic group or combinations thereof, and A is an electron acceptor group; a second electrode; and an electrolyte composition located between the first electrode and the second electrode.

A detailed description is given in the following embodiments with reference to the accompanying drawings.

BRIEF DESCRIPTION OF THE DRAWING

For a more complete understanding of the present invention, and the advantages thereof, reference is now made to the following descriptions taken in conjunction with the accompanying drawings, in which.

DETAILED DESCRIPTION OF THE INVENTION

Figure 1:
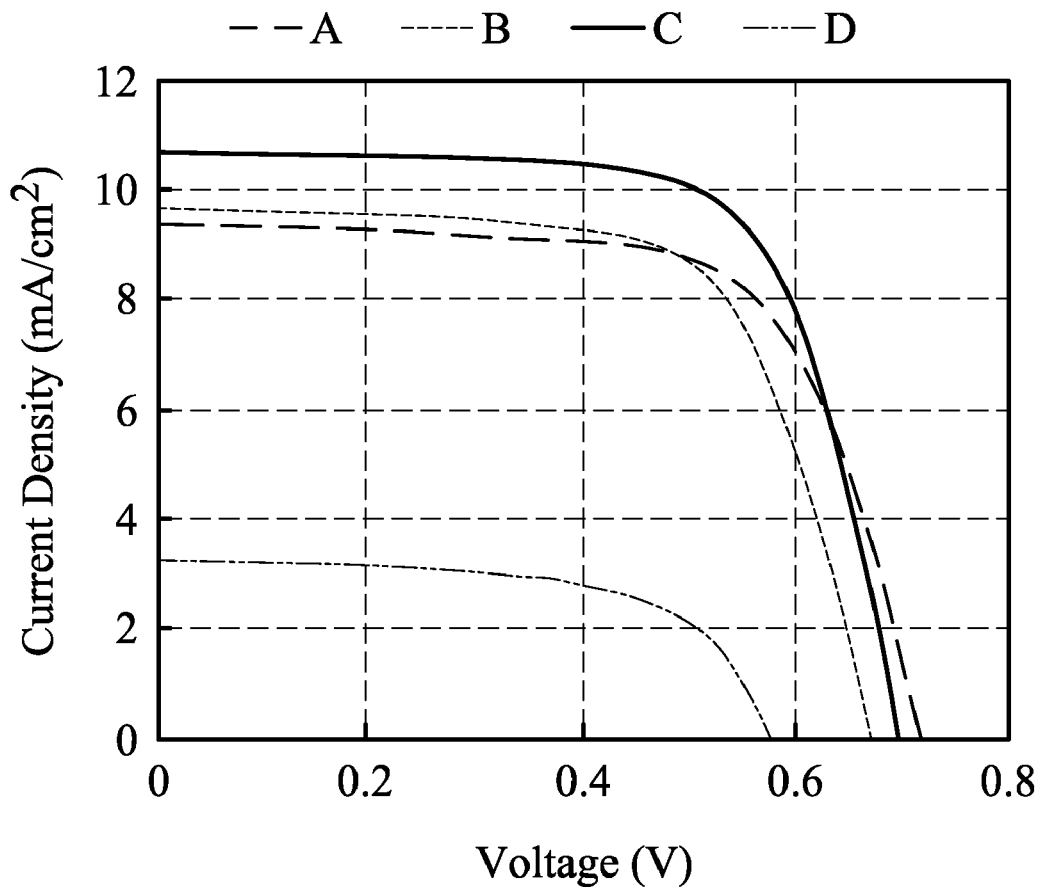
FIG. 1 shows a curve of the voltage as a function of current density of various DSSCs comprising the organic dyes of the invention.

The following description is of the best-contemplated mode of carrying out the invention. This description is made for the purpose of illustrating the general principles of the invention and should not be taken in a limiting sense. The scope of the invention is best determined by reference to the appended claims.

The invention provides an organic dye which has high molar absorption coefficient at about 350 nm-500 nm wavelength regions. The organic dye has a Formula (I):

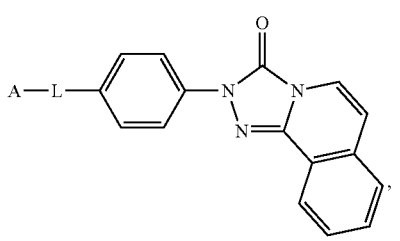

(I)

wherein L is a linker group and comprises a substituted or unsubstituted $C_4$-$C_{20}$ aryl group, a substituted or unsubstituted heteroaryl group, a substituted or unsubstituted carboncyclic group, a substituted or unsubstituted heterocyclic group or combinations thereof, and A is an electron acceptor group.

According to aspects of the invention, L comprises thiophene, vinylthiophene, oligothiophene, bithiophene, quaterthiophene, thienothiophene, dithienothiophene, carbazole, fluorine, dialkyl fluorine, alkyl substituted thiophenes, ethylenedioxythiophene, thienylenevinylene or phenylenevinylene.

According to aspects of the invention, A comprises cyanoacetic acid, rhodanine-3-acetic acid, carboxylic acid, phosphorous acid, sulfonic acid, phosphinic acid, hydroxyl group, oxycarboxylic acid, acid amide, boric acid or squaric acid.

Note that general organic dyes are divided into three parts (abbreviated D-L-A), which comprises an electron donor group (D), a linker group (L) and an electron acceptor group (A), wherein the electron donor group is used to produce an electron, the linker group is used to transfer electron and the electron acceptor group is used to accept electron and transfer the electron to a working electrode of DSSC. The invention provides an organic dye in which [1,2,4]triazolo[3,4-a]isoquinolin-3(2H)-one is used as the electron donor group (D). Compared with general organic metal dye (such as Ru metal complexes), the structure of the invention has longer conjugation length, thus the dye has high molar absorption coefficient at about 350 nm-500 nm wavelength regions.

In one embodiment, the organic dye has a Formula (II):

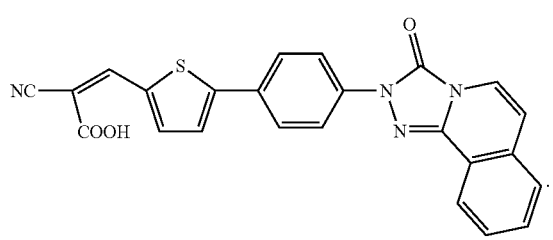

(II)

In another embodiment, the organic dye has a Formula (III):

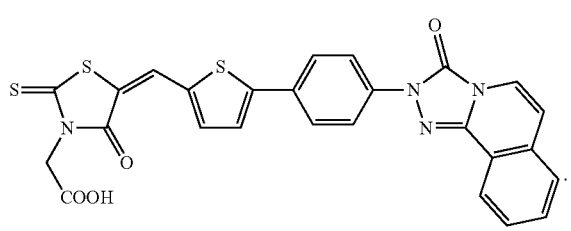

(III)

Since organic dyes of the invention have high molar absorption coefficient at about 350 nm-500 nm wavelength regions, the organic dyes may be used alone, or mixed with other dyes as a co-sensitizer. The other dyes comprise ruthenium (Ru) metal complexes, porphyrin, phthalocyanine, coumarin, cyanine or hemicyanine. The ruthenium (Ru) metal complexes include N3 dye (cis-di(thiocyanato)-bis(2,2'-bipyridyl-4,4'-dicarboxylic acid)-ruthenium(II)), N712 dye $((Bu_4N)_4[R(dcbpy)_2(NCS)_2](Bu_4N$=tetrabutyl-ammonium and dcbpy $H_2$=2,2'-bipyridyl-4,4'-dicarboxylic acid), N719 dye [cis-di(thiocyanato)-bis(2,2'-bipyridyl-4-carboxylate-4'-carboxylic acid)-ruthenium(II)] or N749 dye (4,4',4"-tricarboxy-2,2':6',2'-terpyridine)ruthenium(II)).

Additionally, the invention also provides a composite dye which comprises ruthenium metal complexes and an organic dye having a Formula (I):

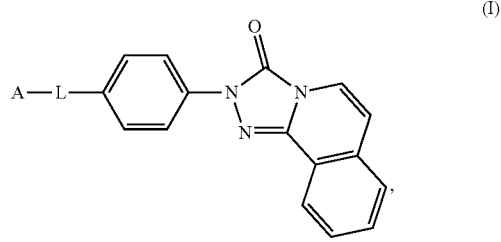

(I)

wherein L is a linker group and comprises a substituted or unsubstituted $C_4$-$C_{20}$ aryl group, a substituted or unsubstituted heteroaryl group, a substituted or unsubstituted carboncyclic group, a substituted or unsubstituted heterocyclic group or combinations thereof, and A is an electron acceptor group. L and A are described above, and thus detailed descriptions are omitted here.

Because the organic dyes of the invention have high molar absorption coefficient at about 350 nm-500 nm wavelength regions, the organic dyes are mixed with the ruthenium metal complexes to improve the performance of the DSSCs. The ruthenium metal complexes and the organic dyes have a molar ratio of 1:0.01 to 1:1.0, and preferably 1:0.05 to 1:0.25).

The composite dye of the invention has several advantages. The organic dyes of the composite dyes are used to compensate for inadequate absorption coefficient of ruthenium metal complexes at 350 nm~500 nm. Additionally, after the ruthenium metal complexes are adsorbed on the working electrode, the vacancy left may be filled by the smaller organic dye to reduce the chance of charge recombination, and further to improve the photoelectric conversion efficiency of a DSSC.

Figure 3:
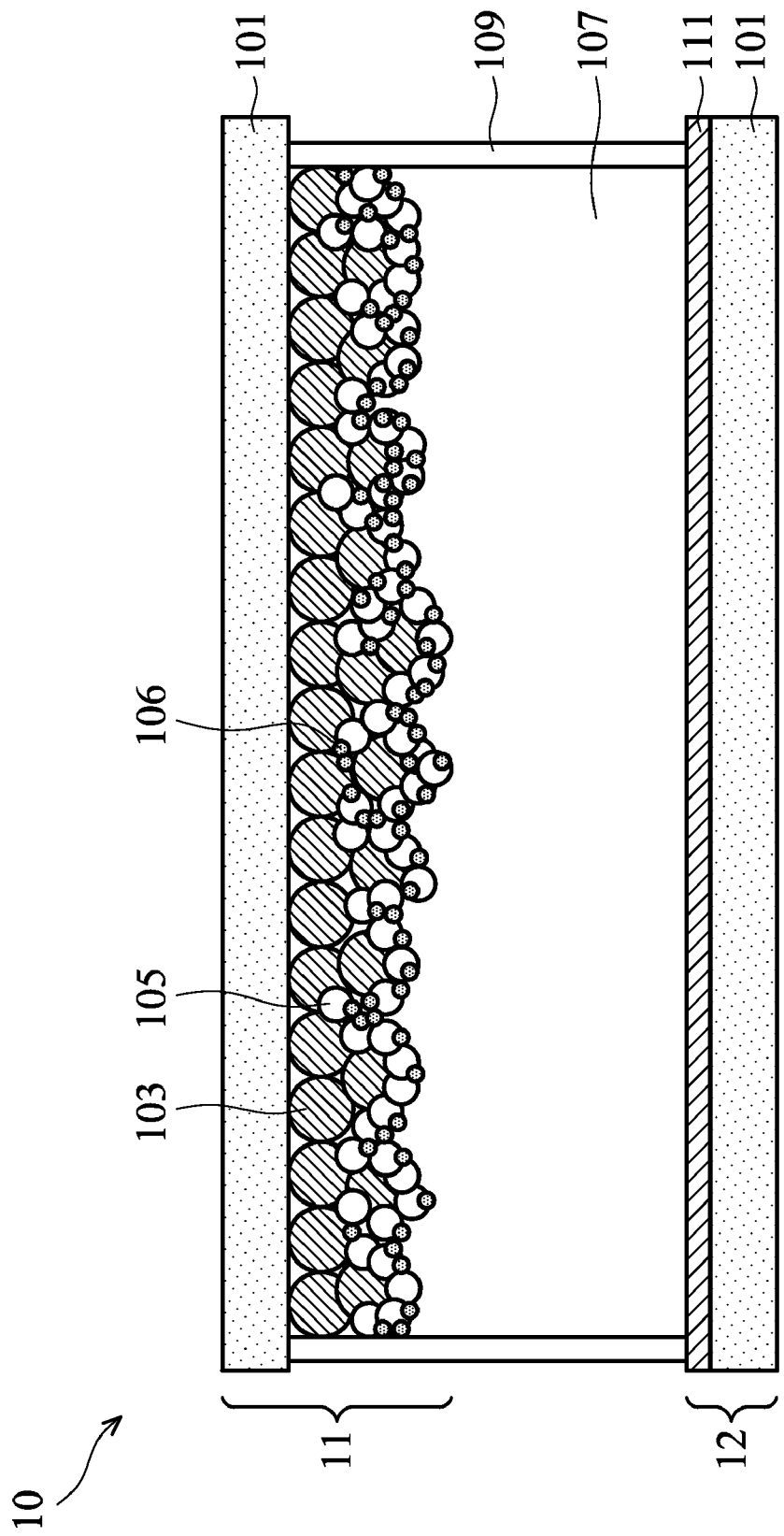
FIG. 3 shows a cross-sectional schematic representation of an DSSC device in accordance with a embodiment of the invention

The invention also provides a DSSC containing the aforementioned organic dyes as a co-sensitizer with ruthenium metal complexes. Referring to FIG. 3, the DSSC 10 comprises a working electrode 11, a counter electrode 12 having a transparent conductive substrate 101 and optionally a platinum (Pt) catalytic layer 111; and an electrolyte composition 107 filled between the working electrode 11 and counter electrode 12. Sealing elements 109 are used as spacers and sealant of DSSC to prevent the electrolyte composition from leaking. The working electrode 11 comprises a transparent conductive substrate 101; a porous $TiO_2$ layer 103 formed on the surface of the transparent conductive substrate 101; and a composite dye carried on the porous $TiO_2$ layer 103, wherein the composite dye comprises ruthenium metal complexes 105 and an organic dye 106 of Formula (I) as previously described.

In one embodiment, the performance of the DSSC comprising the composite dye is as follows: the open circuit voltage ($V_{oc}$) was about 0.6 V-0.7 V; the short current ($J_{sc}$) was about 9 mA/cm$^2$-11 mA/cm$^2$; the fill factor was about 0.5-0.7; and the photoelectric conversion efficiency was about 4%-5.5%.

EXAMPLE

Example 1

(2Z)-2-cyano-3-(5-(4-(3-oxo-[1,2,4]triazolo[3,4-a]isoquinolin-2(3H)-yl)phenyl)thiophen-2-yl)acrylic acid (named as 4L)

The synthesis steps of 4L are shown in Scheme 1.

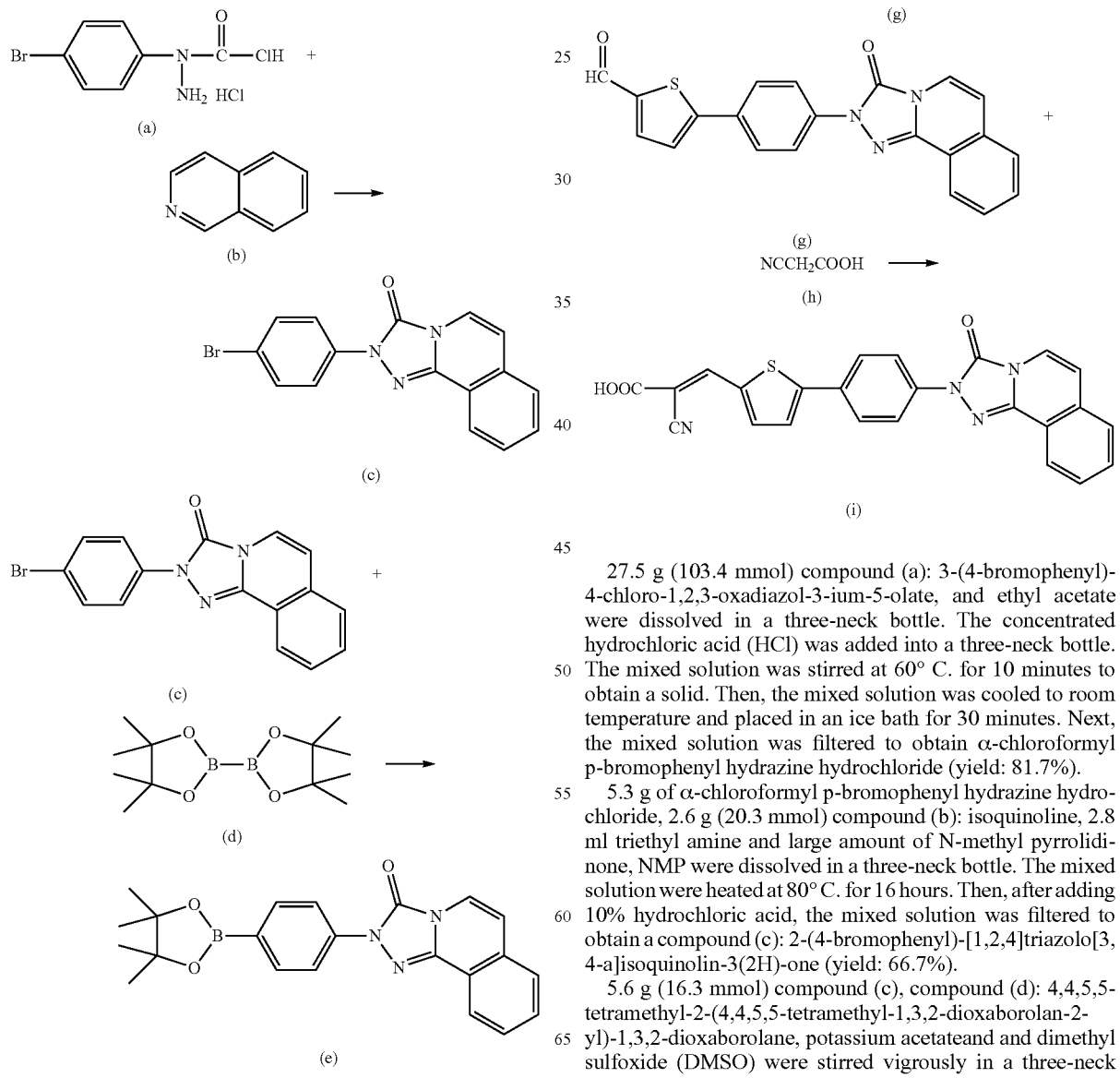

27.5 g (103.4 mmol) compound (a): 3-(4-bromophenyl)-4-chloro-1,2,3-oxadiazol-3-ium-5-olate, and ethyl acetate were dissolved in a three-neck bottle. The concentrated hydrochloric acid (HCl) was added into a three-neck bottle. The mixed solution was stirred at 60° C. for 10 minutes to obtain a solid. Then, the mixed solution was cooled to room temperature and placed in an ice bath for 30 minutes. Next, the mixed solution was filtered to obtain α-chloroformyl p-bromophenyl hydrazine hydrochloride (yield: 81.7%).

5.3 g of α-chloroformyl p-bromophenyl hydrazine hydrochloride, 2.6 g (20.3 mmol) compound (b): isoquinoline, 2.8 ml triethyl amine and large amount of N-methyl pyrrolidinone, NMP were dissolved in a three-neck bottle. The mixed solution were heated at 80° C. for 16 hours. Then, after adding 10% hydrochloric acid, the mixed solution was filtered to obtain a compound (c): 2-(4-bromophenyl)-[1,2,4]triazolo[3,4-a]isoquinolin-3(2H)-one (yield: 66.7%).

5.6 g (16.3 mmol) compound (c), compound (d): 4,4,5,5-tetramethyl-2-(4,4,5,5-tetramethyl-1,3,2-dioxaborolan-2-yl)-1,3,2-dioxaborolane, potassium acetateand and dimethyl sulfoxide (DMSO) were stirred vigorously in a three-neck bottle under an N$_2$ atmosphere. After adding a catalyst of dichloro-[1,1'-bis(diphenylphosphino)ferrocenyl]palladium (II) (Pd(dppf)Cl$_2$), the mixed solution was heated at 80° C. for 6 hours to obtain a compound (e): 2-(4-(4,4,5,5-tetramethyl-1,3,2-dioxaborolan-2-yl)phenyl)-[1,2,4]triazolo[3,4-a]isoquinolin-3(2H)-one (white powder, yield: 84.2%).

1.7 g (4.4 mmol) compound (e), 1.0 g (5.2 mmol) compound (f): 5-bromothiophene-2-carbaldehyde, 2 M potassium carbonate solution and tetrahydrofuran (THF) were stirred vigrously in a three-neck bottle under N$_2$ atmosphere. After adding a catalyst of dichloro-[1,1'-bis(diphenylphosphino)ferrocenyl]palladium(II) (Pd(dppf)Cl$_2$), the mixed solution were heated at 80° C. for 6 hours to obtain a compound (g): 5-(4-(3-oxo-[1,2,4]triazolo[3,4-a]isoquinolin-2(3H)-yl)phenyl)thiophene-2-carbaldehyde (pale yellow powder, yield: 61.6%).

1.2 g (3.3 mmol) compound (g), 0.6 g (6.5 mmol) compound (h): 2-cyanoacetic acid, piperidine and chloroform were dissolved in a three-neck bottle. The mixed solution was refluxed for 16 hours to obtain a product (i): (2Z)-2-cyano-3-(5-(4-(3-oxo-[1,2,4]triazolo[3,4-a]isoquinolin-2(3H)-yl) phenyl) thiophen-2-yl)acrylic acid (pale orange powder, yield: 85.0%).

NMR data of the product (i) was as follows.
$^1$H NMR (300 MHz, d$_6$-DMSO): δ 8.32 (d, 1H, J=7.50 Hz), 8.23 (s, 1H), 8.20 (d, 2H, J=3.20 Hz), 7.93 (d, 2H, J=8.72 Hz), 7.89~7.67 (m, 6H), 7.03 (d, 1H, J=7.46 Hz).

ESI-MS data of compound (i) was 437 (M-H$^+$) m/z.

Example 2

2-(5-(4-(3-oxo-[1,2,4]triazolo[3,4-a]isoquinolin-2(3H)-yl)phenyl)thiophen-2-yl)methylene)-4-oxo-2-thioxothiazolidin-3-yl)acetic acid (name as 4RL)

The synthesis steps of the 4RL are described as follows. 0.7 g (1.9 mmol) compound (g):5-(4-(3-oxo-[1,2,4]triazolo[3,4-a]isoquinolin-2(3H)-yl)phenyl)thiophene-2-carbaldehyde of Example 1, 0.7 g (3.8 mmol) (4-oxo-2-thioxo-thiazolidin-3-yl)-acetic acid (rhodanine-3-acetic acid), piperidine and chloroform were mixed in a three-neck bottle. The mixed solution was refluxed for 16 hours to obtain a product of 2-(5-(4-(3-oxo-[1,2,4]triazolo[3,4-a] isoquinolin-2(3H)-yl)phenyl) thiophen-2-yl)methylene)-4-oxo-2-thioxothiazolidin-3-yl) acetic acid (orange red powder, yield: 95.4%).

NMR data of Example 2 was as follows.
$^1$H NMR (300 MHz, d$_6$-DMSO): δ 8.32 (d, 1H, J=7.60 Hz), 8.22 (d, 2H, J=8.75 Hz), 8.21 (s, 1H), 8.01~7.95 (m, 2H), 7.85~7.67 (m, 6H), 7.04 (d, 2H, J=7.47 Hz), 4.66 (s, 2H).

ESI-MS data of Example 2 was 543 (M-H$^+$) m/z.

Example 3

Example 3 is a dye-sensitized solar cell (DSSC), which comprised: a working electrode; a counter electrode disposed on the opposite side of working electrode; and an electrolyte disposed between the working electrode and the counter electrode. The structure of DSSC of Example 3 is represented as ITO/TiO$_2$/electrolyte/Pt/ITO.

Preparation of the Working Electrode

A cleaned ITO glass was provided. Then, titania pastes (Ti-Nanoxide T/SP series, purchased from Solaronix) and another kind of titania pastes (Ti-Nanoxide R/SP series) were applied to the cleaned ITO (using a doctor blade method), and the ITO was heated at 450° C. to form the working electrode. The thickness of both titanium oxide layers was about 8±4 μm. Subsequently, the working electrode was immersed in a solution comprising dye for 24 hours to absorb the photosensensitive dye. The composition of the dye comprised 4L of Example 1 and N719 (purchased from Solaronix).

Preparation of the Counter Electrode

A Pt counter electrode is formed by a DC sputter method on the ITO glass. The DC sputtering method was performed with a mixture of Ar flow rate of 10 sccm, a pressure of 1 mtorr, a time of 10 second, and a power of 175 W to obtain the counter electrode with a thickness of about 100 nm.

Injection of an Electrolyte and Sealing

The above prepared working electrode and counter electrode were bonded, and an electrolyte comprising 0.6 M 1-propyl-3-methylimidazolium iodide, 0.05M I$_2$ and 3-methoxypropionitrile (MPN) was injected therebetween, and sealed to prepare the DSSC. Additionally, other additives were also added into the electrolyte, such as 0.5 M 4-tert-butylpyridine (TBP), 0.1M guanidinium thiocyanate (GuSCN) and 0.1M LiI.

Table 1 shows the performances of four devices (Device A-D) comprising different dye. As shown in Table 1, the Device C(N719:4 L=1:0.25) had the best photoelectric conversion efficiency.

|  | Device | | | |
| --- | --- | --- | --- | --- |
|  | Device A | Device B | Device C | Device D |
| Dye composition (molar ratio) | Only N719 | N719:4L = 1:1 | N719:4L = 1:0.25 | Only 4L |
| open-circuit voltage (V) | 0.72 | 0.67 | 0.70 | 0.58 |
| short-circuit current (mA/cm$^2$) | 9.36 | 9.66 | 10.68 | 3.25 |
| fill factor | 0.67 | 0.66 | 0.69 | 0.61 |
| photoelectric conversion efficiency (%) | 4.49 | 4.31 | 5.15 | 1.14 |

FIG. 1 shows a curve of the voltage as a function of current density of Device A-D. As shown in FIG. 1, compared to Device A-D, the Device C had the highest current density at the same voltage.

Figure 2:
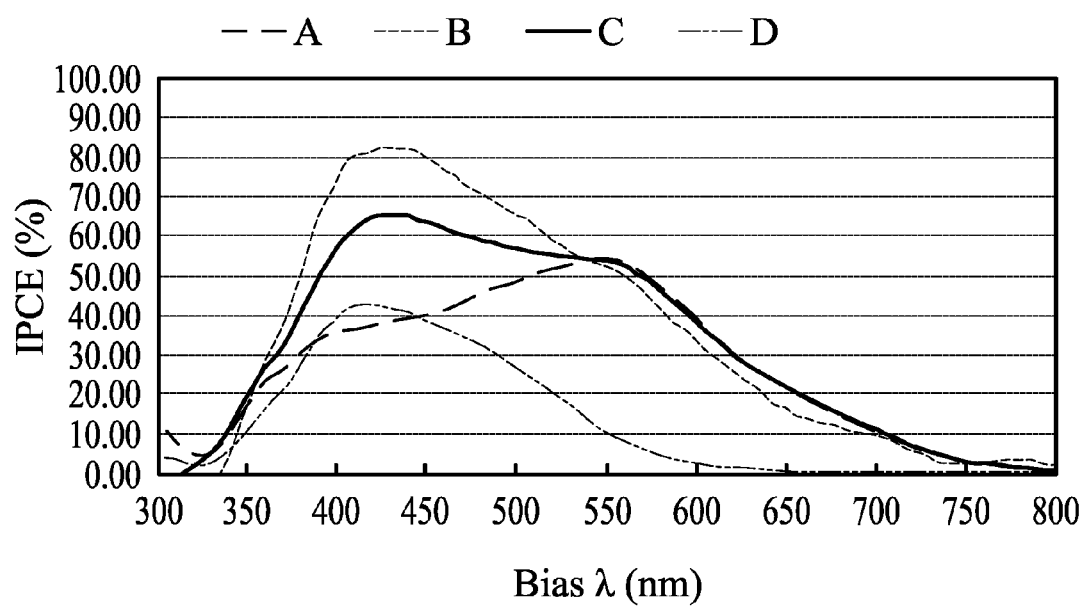
FIG. 2 shows a curve of the bias wavelength as a function of incident photo to the current conversion efficiency (IPCE) of various DSSCs comprising the organic dyes of the invention.

FIG. 2 shows a curve of the bias wavelength as a function of incident photo to the current conversion efficiency (IPCE) of Device A-D. As shown in FIG. 2, Device A has a lower molar absorption coefficient at about 350 nm-500 nm wavelength regions, and the Device B or C has a higher molar absorption coefficient at about 350 nm-500 nm wavelength regions. Thus, the organic dye of the invention was used to compensate for inadequate absorption coefficient of ruthenium metal complexes at 350 nm~500 nm to improve the photoelectric conversion efficiency of DSSC.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An organic dye having Formula (I):

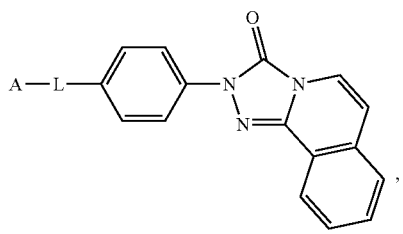

wherein L is a linker group comprising a substituted or unsubstituted $C_4$-$C_{20}$ aryl group, a substituted or unsubstituted heteroaryl group, a substituted or unsubstituted carboncyclic group, a substituted or unsubstituted heterocyclic group or combinations thereof, and A is an electron acceptor group.

2. The organic dye as claimed in claim 1, wherein L comprises thiophene, vinylthiophene, oligothiophene, bithiophene, quaterthiophene, thienothiophene, dithienothiophene, carbazole, fluorine, dialkyl fluorine, alkyl substituted thiophenes, ethylenedioxythiophene, thienylenevinylene or phenylenevinylene.

3. The organic dye as claimed in claim 1, wherein A comprises cyanoacetic acid, rhodanine-3-acetic acid, carboxylic acid, phosphorous acid, sulfonic acid, phosphinic acid, hydroxyl group, oxycarboxylic acid, acid amide, boric acid or squaric acid.

4. The organic dye as claimed in claim 1, wherein the organic dye has Formula (II):

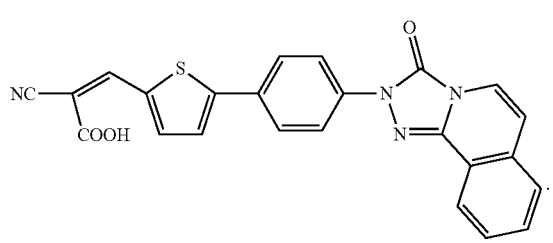

5. The organic dye as claimed in claim 1, wherein the organic dye has Formula (III):

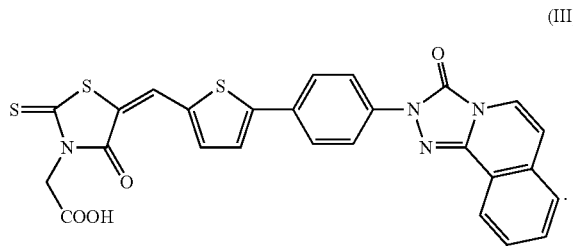

6. The organic dye as claimed in claim 1, further comprising ruthenium metal complexes, porphyrin, phthalocyanine, coumarin, cyanine or hemicyanine.

7. The organic dye as claimed in claim 6, wherein the ruthenium metal complexes comprises cis-di(thiocyanato)-bis(2,2'-bipyridyl-4,4'-dicarboxylic acid)-ruthenium(II), $(Bu_4N)_4[R(dcbpy)_2(NCS)_2]$ ($Bu_4N$=tetrabutyl-ammonium and dcbpy $H_2$=2,2'-bipyridyl-4,4'-dicarboxylic acid, [cis-di(thiocyanato)-bis(2,2'-bipyridyl-4-carboxylate-4'-carboxylic acid)-ruthenium(II)] or (4,4',4"-tricarboxy-2,2':6',2'-terpyridine)ruthenium(II)).

8. A composite dye, comprising:
ruthenium metal complexes; and
an organic dye having Formula (I):

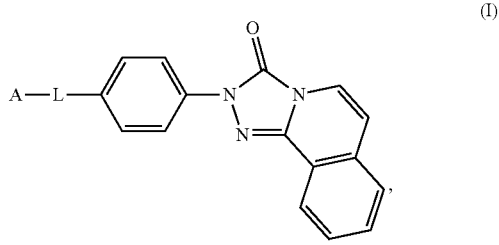

wherein L is a linker group comprising a substituted or unsubstituted $C_4$-$C_{20}$ aryl group, a substituted or unsubstituted heteroaryl group, a substituted or unsubstituted carboncyclic group, a substituted or unsubstituted heterocyclic group or combinations thereof, and A is an electron acceptor group.

9. The composite dye as claimed in claim 8, wherein the ruthenium metal complexes and the organic dye have a molar ratio from 1:0.01 to 1:1.0.

10. The composite dye as claimed in claim 8, wherein L comprises thiophene, vinylthiophene, oligothiophene, bithiophene, quaterthiophene, thienothiophene, dithienothiophene, carbazole, fluorine, dialkyl fluorine, alkyl substituted thiophenes, ethylenedioxythiophene, thienylenevinylene or phenylenevinylene.

11. The composite dye as claimed in claim 8, wherein A comprises cyanoacetic acid, rhodanine-3-acetic acid, carboxylic acid, phosphorous acid, sulfonic acid, phosphinic acid, hydroxyl group, oxycarboxylic acid, acid amide, boric acid or squaric acid.

12. The composite dye as claimed in claim 8, wherein the organic dye has Formula (II):

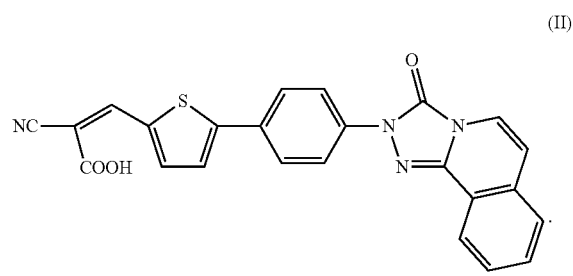 [SMILES: N#C/C(=C/c1ccc(-c2ccc(-n3nc4c5ccccc5ccn4c3=O)cc2)s1)C(=O)O]

13. The composite dye as claimed in claim 8, wherein the organic dye has Formula (III):

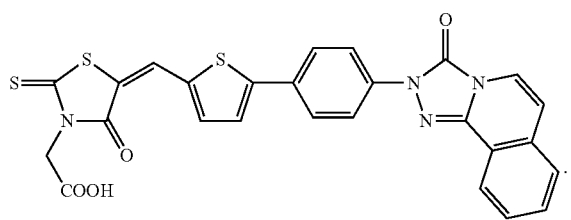
(III)

14. A dye-sensitized solar cell comprising:
a first electrode, wherein the first electrode comprises a composite dye and the composite dye comprises:
ruthenium metal complexes; and
an organic dye having Formula (I):

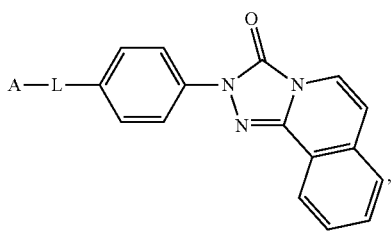
(I)

wherein L is a linker group comprising a substituted or unsubstituted $C_4$-$C_{20}$ aryl group, a substituted or unsubstituted heteroaryl group, a substituted or unsubstituted carboncyclic group, a substituted or unsubstituted heterocyclic group or combinations thereof, and A is an electron acceptor group;
a second electrode; and
an electrolyte composition formed between the first electrode and the second electrode.

15. The dye-sensitized solar cell as claimed in claim 14, wherein L comprises thiophene, vinylthiophene, oligothiophene, bithiophene, quaterthiophene, thienothiophene, dithienothiophene, carbazole, fluorine, dialkyl fluorine, alkyl substituted thiophenes, ethylenedioxythiophene, thienylenevinylene or phenylenevinylene.

16. The dye-sensitized solar cell as claimed in claim 14, wherein A comprises cyanoacetic acid, rhodanine-3-acetic acid, carboxylic acid, phosphorous acid, sulfonic acid, phosphinic acid, hydroxyl group, oxycarboxylic acid, acid amide, boric acid or squaric acid.

17. The dye-sensitized solar cell as claimed in claim 14, wherein the organic dye has Formula (II):

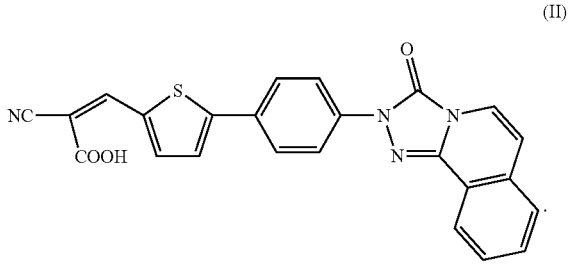 [SMILES: N#C/C(=C/c1ccc(-c2ccc(-n3nc4c5ccccc5ccn4c3=O)cc2)s1)C(=O)O]
(II)

18. The dye-sensitized solar cell as claimed in claim 14, wherein the organic dye has Formula (III):

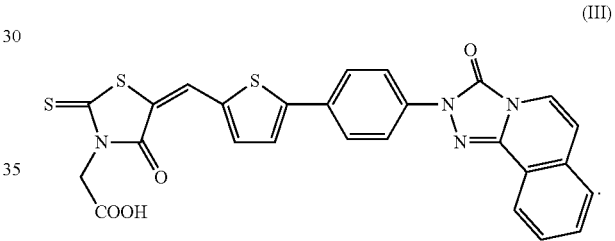
(III)

* * * * *